(12) United States Patent
Lin et al.

(10) Patent No.: US 11,800,985 B2
(45) Date of Patent: Oct. 31, 2023

(54) ELECTROCARDIOGRAPHIC MONITORING DEVICE AND BLOOD PRESSURE MONITORING SYSTEM USING THE SAME

(71) Applicants: BIV MEDICAL, LTD., Caotun Township, Nantou County (TW); Shiming Lin, Taipei (TW)

(72) Inventors: Shiming Lin, Taipei (TW); Shih-Wei Chiang, Taipei (TW); Cheng-Yan Guo, Taipei (TW); Tai-Cun Lin, Taipei (TW); Wei-Chih Huang, Taipei (TW); Chun-Nan Chen, Taipei (TW); Ya-Ting Chang, Taipei (TW)

(73) Assignees: Shiming Lin, Taipei (TW); BIV MEDICAL, LTD., Nantou County (TW)

( * ) Notice: Subject to any disclaimer, the term of this patent is extended or adjusted under 35 U.S.C. 154(b) by 566 days.

(21) Appl. No.: 16/465,370

(22) PCT Filed: Nov. 30, 2017

(86) PCT No.: PCT/CN2017/113922
§ 371 (c)(1),
(2) Date: May 30, 2019

(87) PCT Pub. No.: WO2018/099426
PCT Pub. Date: Jun. 7, 2018

(65) Prior Publication Data
US 2019/0387984 A1 Dec. 26, 2019

Related U.S. Application Data

(60) Provisional application No. 62/604,137, filed on Jun. 26, 2017, provisional application No. 62/498,991,
(Continued)

(51) Int. Cl.
*A61B 5/00* (2006.01)
*A61B 5/021* (2006.01)
(Continued)

(52) U.S. Cl.
CPC ........ *A61B 5/02108* (2013.01); *A61B 5/0006* (2013.01); *A61B 5/02116* (2013.01);
(Continued)

(58) Field of Classification Search
CPC ....... A61B 5/02108; A61B 5/332; A61B 5/30; A61B 5/282; A61B 5/0006;
(Continued)

(56) References Cited

U.S. PATENT DOCUMENTS

| 4,676,253 A | 6/1987 | Newman et al. |
| 2007/0287923 A1* | 12/2007 | Adkins .................. A61B 5/022 600/485 |

(Continued)

FOREIGN PATENT DOCUMENTS

| CN | 1548005 A | 11/2004 |
| CN | 204306822 U | 5/2015 |

(Continued)

*Primary Examiner* — Adam Z Minchella
(74) *Attorney, Agent, or Firm* — Muncy, Geissler, Olds & Lowe, P.C.

(57) ABSTRACT

The present invention provides an electrocardiographic monitoring device comprising a device body configured to be attached to a user's chest; a plurality of electrodes provided on the device body; and a controller provided on the device body and connected to the electrodes in order to obtain the user's electrocardiographic signal waveforms. The electrocardiographic monitoring device of the invention can be applied in a blood pressure monitoring system for monitoring a user's blood pressure.

9 Claims, 11 Drawing Sheets

Related U.S. Application Data filed on Jan. 13, 2017, provisional application No. 62/497,741, filed on Dec. 1, 2016, provisional application No. 62/497,740, filed on Dec. 1, 2016.

(51) Int. Cl.
| | |
|---|---|
| *A61B 5/25* | (2021.01) |
| *A61B 5/024* | (2006.01) |
| *A61B 5/022* | (2006.01) |
| *A61B 7/04* | (2006.01) |
| *A61B 5/30* | (2021.01) |
| *A61B 5/282* | (2021.01) |
| *A61B 5/332* | (2021.01) |

(52) U.S. Cl.
CPC ...... *A61B 5/02225* (2013.01); *A61B 5/02438* (2013.01); *A61B 5/02444* (2013.01); *A61B 5/282* (2021.01); *A61B 5/30* (2021.01); *A61B 5/332* (2021.01); *A61B 5/681* (2013.01); *A61B 5/6823* (2013.01); *A61B 5/6824* (2013.01); *A61B 5/6841* (2013.01); *A61B 7/04* (2013.01); *A61B 5/02416* (2013.01); *A61B 5/25* (2021.01); *A61B 2562/0204* (2013.01); *A61B 2562/0209* (2013.01); *A61B 2562/0247* (2013.01)

(58) Field of Classification Search
CPC ............ A61B 5/02116; A61B 5/02225; A61B 5/02438; A61B 5/02444; A61B 5/681; A61B 5/6823; A61B 5/6824; A61B 5/6841; A61B 7/04; A61B 5/25; A61B 5/02416; A61B 2562/0204; A61B 2562/0209; A61B 2562/0247

See application file for complete search history.

(56) References Cited

U.S. PATENT DOCUMENTS

| | | | |
|---|---|---|---|
| 2009/0326400 A1* | 12/2009 | Huldt | A61B 5/68 600/509 |
| 2016/0143546 A1* | 5/2016 | McCombie | A61B 5/02125 600/494 |
| 2016/0296171 A1* | 10/2016 | Drori | A61B 5/1072 |
| 2016/0374615 A1* | 12/2016 | Tsukada | D06M 15/3566 600/382 |
| 2017/0258402 A1* | 9/2017 | Acquista | A61B 5/6833 |

FOREIGN PATENT DOCUMENTS

| | | |
|---|---|---|
| CN | 205144537 U | 4/2016 |
| CN | 105592782 A | 5/2016 |
| CN | 105726011 A | 7/2016 |
| CN | 105939660 A | 9/2016 |

\* cited by examiner

ELECTROCARDIOGRAPHIC MONITORING DEVICE AND BLOOD PRESSURE MONITORING SYSTEM USING THE SAME

BACKGROUND OF THE INVENTION

1. Technical Field

The present invention relates to an electrocardiographic monitoring device. More particularly, the invention relates to an electrocardiographic monitoring device for use in 24-hour blood pressure monitoring so as to monitor a user's blood pressure variation over time.

2. Description of Related Art 24-hour ambulatory blood pressure monitoring contributes significantly to the prevention of hypertension. By measuring a person's blood pressure ambulatorily, errors that sporadic incidents (e.g., an outburst of emotion, drinking, eating, or smoking) may cause to the person's blood pressure measurements can be recorded in real time to facilitate tracking. More importantly, an analysis of the data obtained by monitoring a patient's blood pressure in an ambulatory manner helps reveal the patient's health condition and determine in advance whether the patient is prone to hypertension or prehypertension.

Thanks to the advancement of technology, sphygmomanometers have been downsized for household use or for incorporation into a wearable device so that a user can monitor their blood pressure whenever desired. Wearable blood pressure monitoring devices, in particular, have progressed so much that changes in blood pressure can be detected at any time simply by attaching sensors to the body and connecting the sensors to a wearable device. For example, Chinese Published Invention Patent Application No. 106419980A discloses a wearable blood pressure device that includes electrodes and a wearable wrist device. The electrodes are attachable to a user's chest in order to detect electrocardiographic signals. The wrist device is used to detect pulse waves, calculate blood pressure from the detection results, and thereby obtain blood pressure parameters. This blood pressure device can provide 24-hour monitoring of a user's blood pressure variation.

Today, many a wearable blood pressure monitoring device has been developed to monitor a user's blood pressure variation around the clock, but the existing wearable blood pressure monitoring devices are disadvantaged by inconveniences of use. Basically, a wearable blood pressure monitoring device works by sensing and measuring the waveforms of electrocardiographic signals and of pulse signals and then computing on the waveform measurements to obtain blood pressure values. It is therefore required that a plurality of electrodes be attached to a user's chest to sense the electrocardiographic signal waveforms, and that a pulse wave sensing device be provided at the user's arm or wrist to sense the pulse signal waveforms. As the electrodes of a conventional wearable blood pressure monitoring device are generally designed to be attached to the skin of the chest in a distributed manner, a user has to place the electrodes at the required sensing positions one after another, which can be troublesome. Moreover, an erroneous arrangement of the electrodes will cause noise in the measuring process, and should the R-wave peak values of electrocardiographic signals be interfered by noise, it will be impossible to measure pulse wave velocity and electrocardiographic signal waveforms accurately, let alone blood pressure values. In addition, the wires connecting the electrodes to the pulse sensing device tend to cause an uncomfortable sensation to a user wearing the blood pressure monitoring device, and may be disconnected at either end when the user moves.

BRIEF SUMMARY OF THE INVENTION

One objective of the present invention is to provide an electrocardiographic monitoring device and a blood pressure monitoring system using the same so as to enhance the comfortableness and accuracy of wearable blood pressure monitoring devices in general.

In order to achieve the above objective, the present invention provides an electrocardiographic monitoring device, comprising: a device body configured to be attached to a user's chest; a plurality of electrodes provided on the device body, wherein the electrodes comprise a right electrode (RA), a left electrode (LA), and a grounding electrode (G), the right electrode and the left electrode are provided on a right side and a left side of the device body respectively, and the grounding electrode is adjacent to the right electrode but is not between the right electrode and the left electrode; and a controller provided on the device body and connected to the electrodes in order to obtain the user's electrocardiographic signal waveforms.

Furthermore, the controller transmits the electrocardiographic signal waveforms obtained to a third-party controller through a wireless transmission module.

Another objective of the present invention is to provide a blood pressure monitoring system, comprising: an electrocardiographic monitoring device configured to be attached to a user's chest, wherein the electrocardiographic monitoring device comprises a device body and a plurality of electrodes provided on the device body to obtain electrocardiographic signal waveforms; and a pulse detection device configured to be worn on a user's limb at a position corresponding to a radial artery, wherein the pulse detection device comprises a sensor for obtaining pulse signal waveforms; wherein at least one selected from the group consisting of the electrocardiographic monitoring device, the pulse detection device, and a mobile device is provided with a controller for calculating the user's blood pressure parameters according to the electrocardiographic signal waveforms and the pulse signal waveforms; and wherein the electrocardiographic monitoring device, the pulse detection device, and the mobile device are connected to one another through wireless transmission.

Furthermore, the electrodes arranged on the device body at least include a right electrode (RA), a left electrode (LA), and a grounding electrode (G). The right electrode (RA) and the left electrode (LA) are placed on the right side and the left side of the device body respectively, and the grounding electrode (G) is adjacent to the right electrode (RA) but does not lie between the right electrode (RA) and the left electrode (LA).

Furthermore, the device body further comprises a positioning mark and a grid, and the positioning mark is intended to coincide with, or be placed right above, the user's xiphoid process.

Furthermore, when the electrocardiographic monitoring device has been attached to a user's chest, the right electrode (RA) and the grounding electrode (G) are horizontally arranged in an area higher than and to the right of the user's xiphoid process, and the left electrode (LA) is higher than and to the left of the user's xiphoid process and is horizontally aligned with the right electrode (RA) and the grounding electrode (G).

Furthermore, when the electrocardiographic monitoring device has been attached to a user's chest, the right electrode (RA) and the grounding electrode (G) are horizontally arranged in an area higher than and to the right of the user's xiphoid process, and the left electrode (LA) is higher than and to the left of the user's xiphoid process and is lower than the right electrode (RA) and the grounding electrode (G).

Furthermore, when the electrocardiographic monitoring device has been attached to a user's chest, the right electrode (RA) and the grounding electrode (G) are vertically arranged in an area higher than and to the right of the user's xiphoid process, with the right electrode (RA) higher than the grounding electrode (G), and the left electrode (LA) is higher than and to the left of the user's xiphoid process and is horizontally aligned with the grounding electrode (G).

Comparing to the conventional techniques, the present invention has the following advantages:

1. The electrocardiographic monitoring device of the present invention is a structure with a plurality of electrodes and is configured for wireless transmission. Once the electrocardiographic monitoring device is attached to a user's chest, the electrodes will not shift in position due to the user's movement; in other words, the waveforms of electrocardiographic signals will not be affected when the user moves.
2. The electrocardiographic monitoring device of the present invention and a blood pressure monitoring system using the same can transmit electrocardiographic signal waveforms and pulse signal waveforms to a blood pressure calculation unit wirelessly, and this is a far cry from the prior art, in which the wires required for data transmission may cause an uncomfortable sensation to a user wearing the device or be caught by accident such that unstable transmission occurs and affects the blood pressure values monitored.
3. The electrocardiographic monitoring device of the present invention and a blood pressure monitoring system using the same can provide 24-hour monitoring of blood pressure variation and are suitable for use at home as well as in emergency rooms, preoperative/postoperative intensive care units, hospital wards, clinics, and other medical institutions.

DETAILED DESCRIPTION OF THE INVENTION

Figure 1:
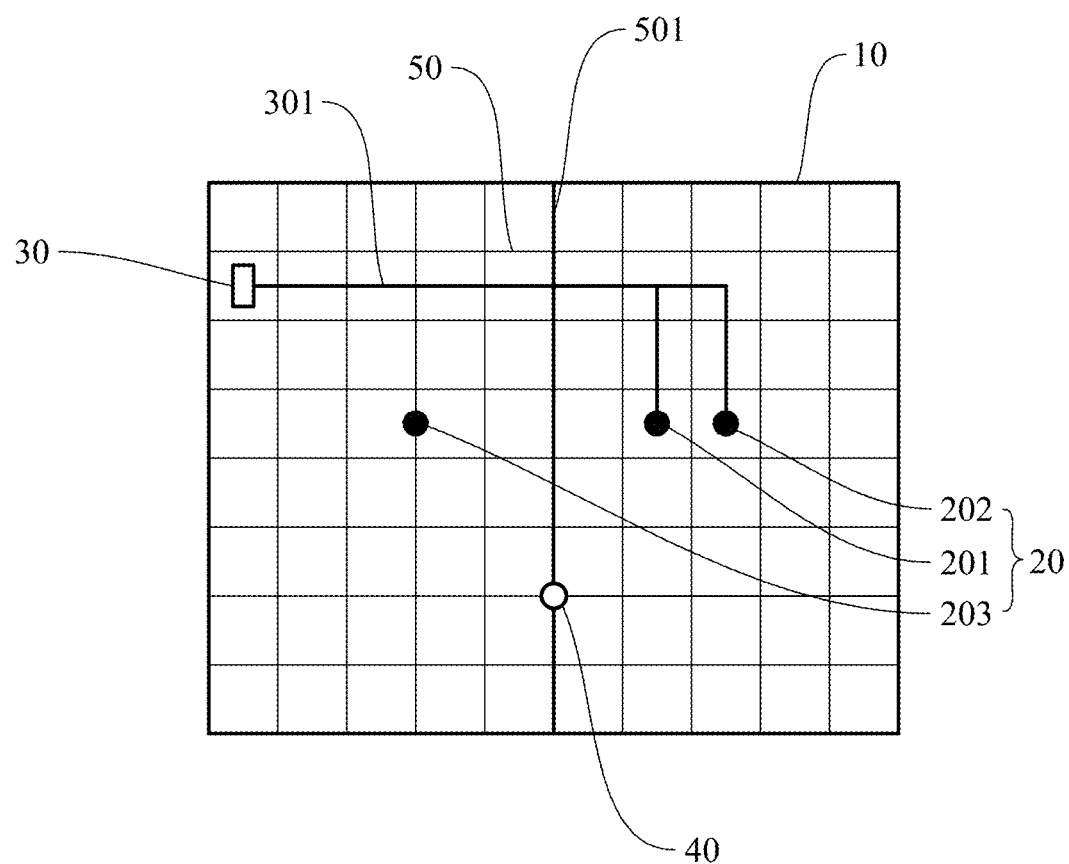
FIG. 1 is a perspective view of the electrocardiographic monitoring device according to the present invention.

The details and technical solution of the present invention are hereunder described with reference to accompanying drawings. For illustrative sake, the accompanying drawings are not drawn to scale. The accompanying drawings and the scale thereof are not restrictive of the present invention.

Please refer to FIG. 1 to FIG. 4, which show the appearance of an electrocardiographic monitoring device according to the present invention and how the device is used.

As shown in the drawings, the electrocardiographic monitoring device 100 includes a device body 10, a plurality of electrodes 20, and a controller 30.

The device body 10 is configured to be attached to a user's chest and has a positioning mark 40 and a grid 50 on both sides of the device body 10. The positioning mark 40 is intended to coincide with, or be placed right above, the user's xiphoid process. The grid 50 includes a vertical auxiliary line 501 passing through the positioning mark 40. To use the electrocardiographic monitoring device 100, the positioning mark 40 and the vertical auxiliary line 501 are respectively aligned with the user's xiphoid process and the centerline of the user's body, and then the electrodes 20 are arranged on the device body 10 according to the grid 50, which serves as a reference coordinate system. After that, the electrocardiographic monitoring device 100 is attached to the user's chest, with the positioning mark 40 and the vertical auxiliary line 501 aligned respectively with the user's xiphoid process and the centerline of the user's body, so that measurement of electrocardiographic signals can begin.

Figure 2:
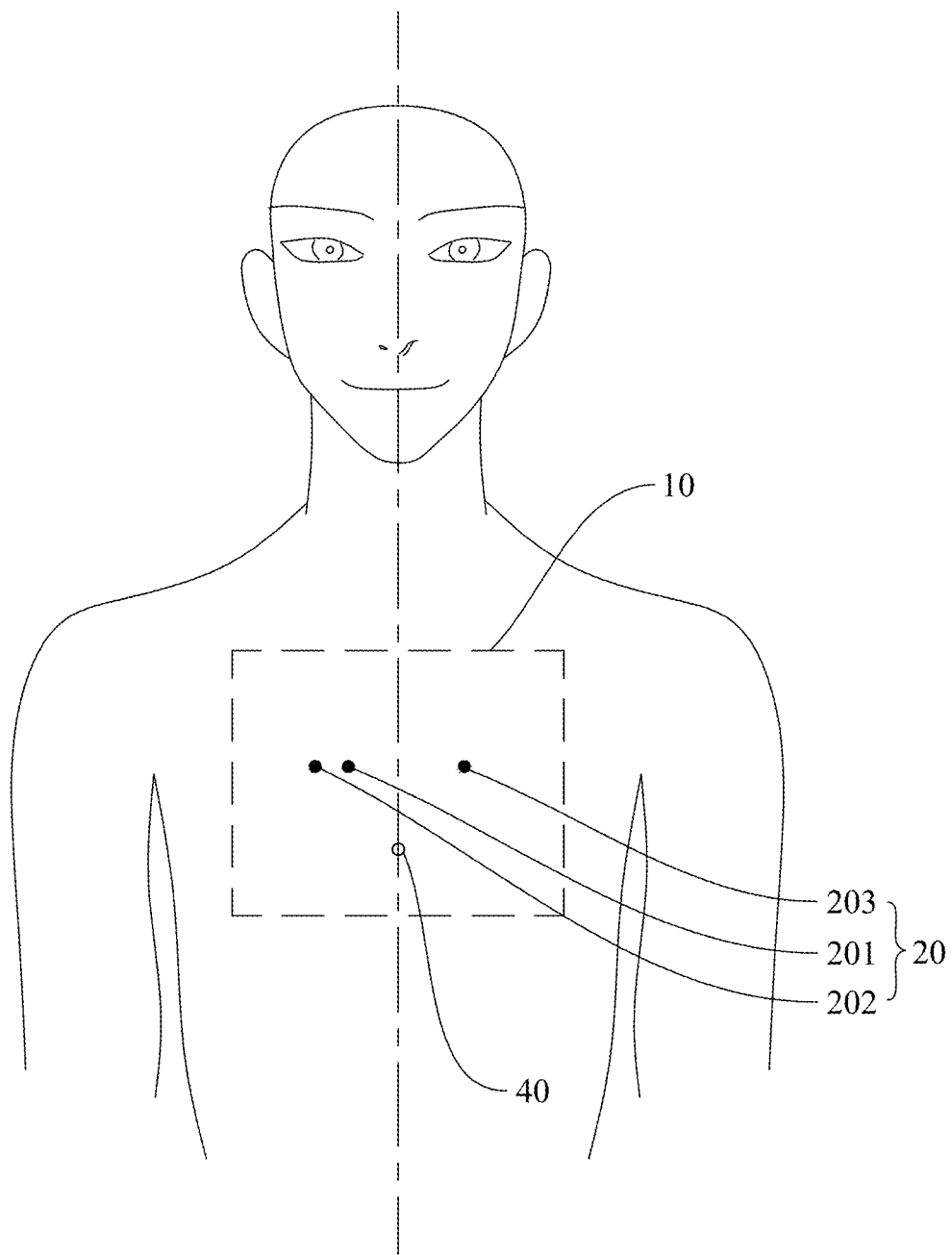
FIG. 2 shows how the electrocardiographic monitoring device according to the present invention is used.

The electrodes 20 arranged on the device body 10 at least include a right electrode (RA) 201, a left electrode (LA) 203, and a grounding electrode (G) 202. The right electrode (RA) 201 and the left electrode (LA) 203 are placed on the right side and the left side of the device body 10 respectively, as shown in FIG. 1, in which the right side of the electrocardiographic monitoring device 100 corresponds to a user's right side (from the user's point of view), as shown in FIG. 2, and the left side of the electrocardiographic monitoring device 100 corresponds to the user's left side (also from the user's point of view), as shown in FIG. 2. The grounding electrode (G) 202 is adjacent to the right electrode (RA) 201 but does not lie between the right electrode (RA) 201 and the left electrode (LA) 203.

The controller 30 is provided on the device body 10 and is connected to the electrodes 20 by a connecting circuit 301 in order to obtain a user's electrocardiographic signal waveforms. The controller 30 can further transmit the electrocardiographic signal waveforms obtained to a third-party controller through a wireless transmission module. The third-party controller may be a pulse detection device 60 worn on the wrist (see FIG. 3 and FIG. 4) or a mobile device 70 (e.g., a smartphone or tablet computer, as shown in FIG. 4) without limitation. For example, the controller 30 may be coupled to the pulse detection device 60 on a user's wrist through a wireless transmission module so that the user's blood pressure parameters can be calculated by the controller 30, the pulse detection device 60, or the mobile device 70 (which is wirelessly connected to the controller 30 and the pulse detection device 60) according to the electrocardiographic signal waveforms obtained by the controller 30 and the pulse signal waveforms obtained by the pulse detection device 60; in other words, computation on the electrocardiographic signal waveforms may be performed by the controller 30, the pulse detection device 60, or the mobile device 70. The electrocardiographic monitoring device 100, therefore, can work either with the pulse detection device 60 or with the pulse detection device 60 and the mobile device 70.

The wireless transmission module may use one or a combination of the following protocols/techniques: Bluetooth, infrared (IR) transmission, near-field communication (NFC), ultra-wideband (UWB), wireless local area networks (WLAN), Wireless Gigabit Alliance (WiGig Alliance) communications technology, ZigBee, wireless universal serial bus (wireless USB), and Wi-Fi; the present invention has no limitation in this regard.

In this embodiment, the pulse detection device 60 to be worn on a user's wrist is in the form of a watch, but it is also feasible to implement the pulse detection device 60 as a health bracelet or sports bracelet instead of a watch; the present invention has no limitation in this regard. The pulse detection device 60 may be provided with software, such as a mobile application (app), for processing electrocardiographic signal waveforms, pulse signal waveforms, and blood pressure parameters, in order to compute on, record, and display the electrocardiographic signal waveforms, pulse signal waveforms, and blood pressure parameters.

In this embodiment, the mobile device 70 is in the form of a mobile phone, but it is also feasible to implement the mobile device 70 as a tablet computer or laptop computer instead of a mobile phone; the present invention has no limitation in this regard. The mobile device 70 may be provided with software, such as an app, for processing electrocardiographic signal waveforms, pulse signal waveforms, and blood pressure parameters, in order to compute on, record, and display the electrocardiographic signal waveforms, pulse signal waveforms, and blood pressure parameters.

In addition, the controller 30, the pulse detection device 60 to be worn on a user's wrist, and the mobile device 70 may be provided with a storage unit for recording electrocardiographic signal waveforms, pulse signal waveforms, and blood pressure parameters. The storage unit may be a memory card or other devices with a memory function, such as a compact flash card (CF card), a secure digital card (SD card), a multimedia card, a smart media card (SM card), a memory stick (MS card), or a mini secure digital card (mini SD card). The present invention has no limitation on the type of the storage unit.

FIG. 5 to FIG. 10 show three ways to arrange the electrodes on the electrocardiographic monitoring device of the present invention and the resulting electrocardiographic signal waveforms.

Figure 5:
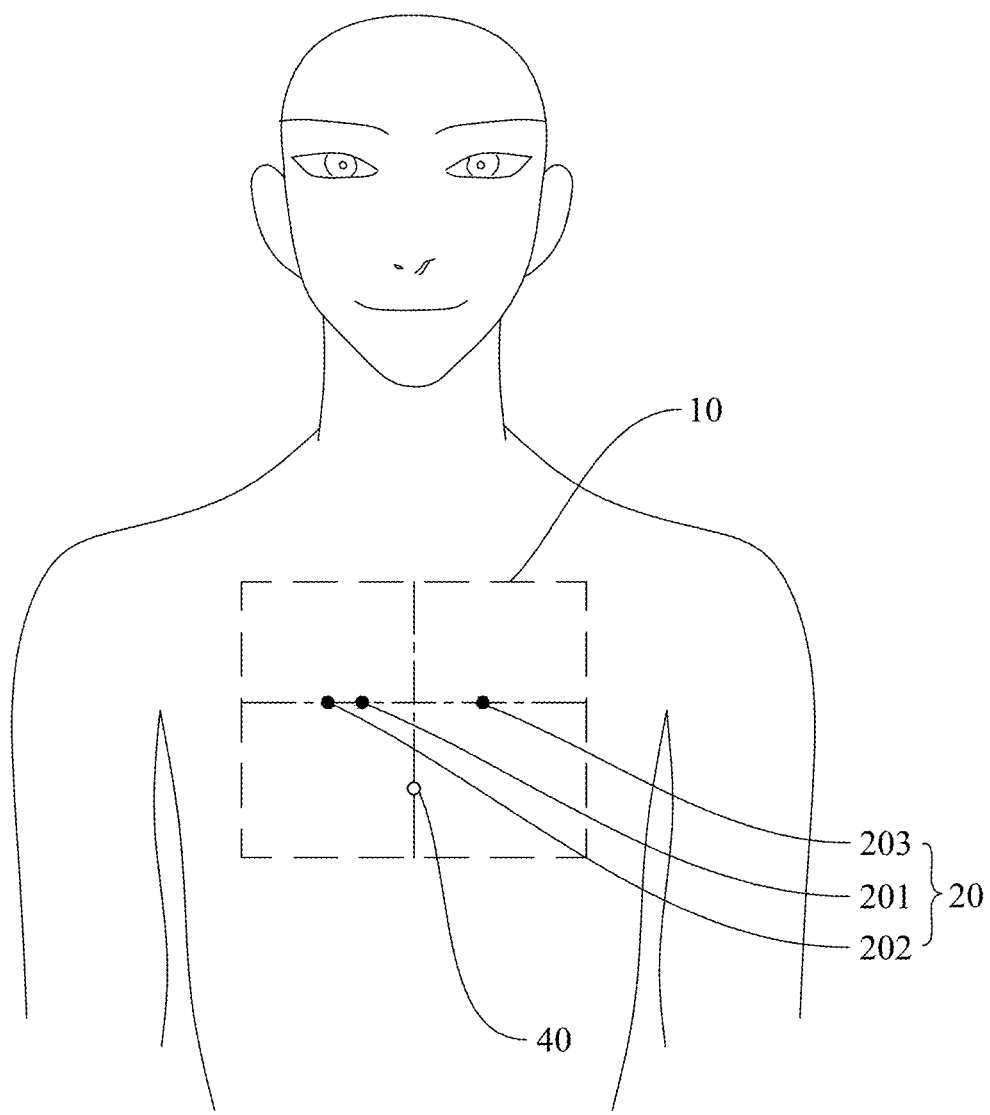
FIG. 5 shows a method (I) of arranging the electrodes on the electrocardiographic monitoring device of the present invention.
Figure 6:
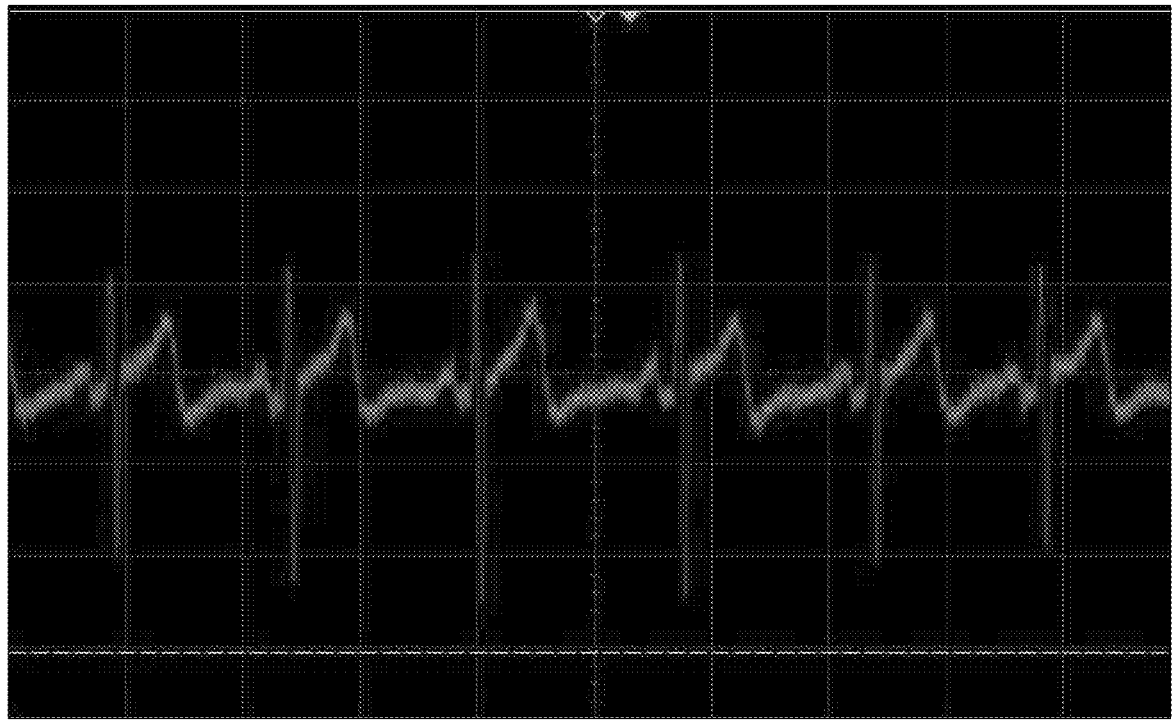
FIG. 6 shows a first group of electrocardiographic signal waveforms resulting from the method (I) of arranging the electrodes on the electrocardiographic monitoring device of the present invention.

In the preferred embodiment shown in FIG. 5, in which the electrocardiographic monitoring device 100 has been attached to a user's chest, the right electrode (RA) 201 and the grounding electrode (G) 202 are horizontally arranged in an area higher than and to the right of the user's xiphoid process 401 (from the user's point of view), and the left electrode (LA) 203 is higher than and to the left of the user's xiphoid process 401 (also from the user's point of view) and is horizontally aligned with the right electrode (RA) 201 and the grounding electrode (G) 202. This electrode arrangement produces an electrocardiogram as shown in FIG. 6.

Figure 7:
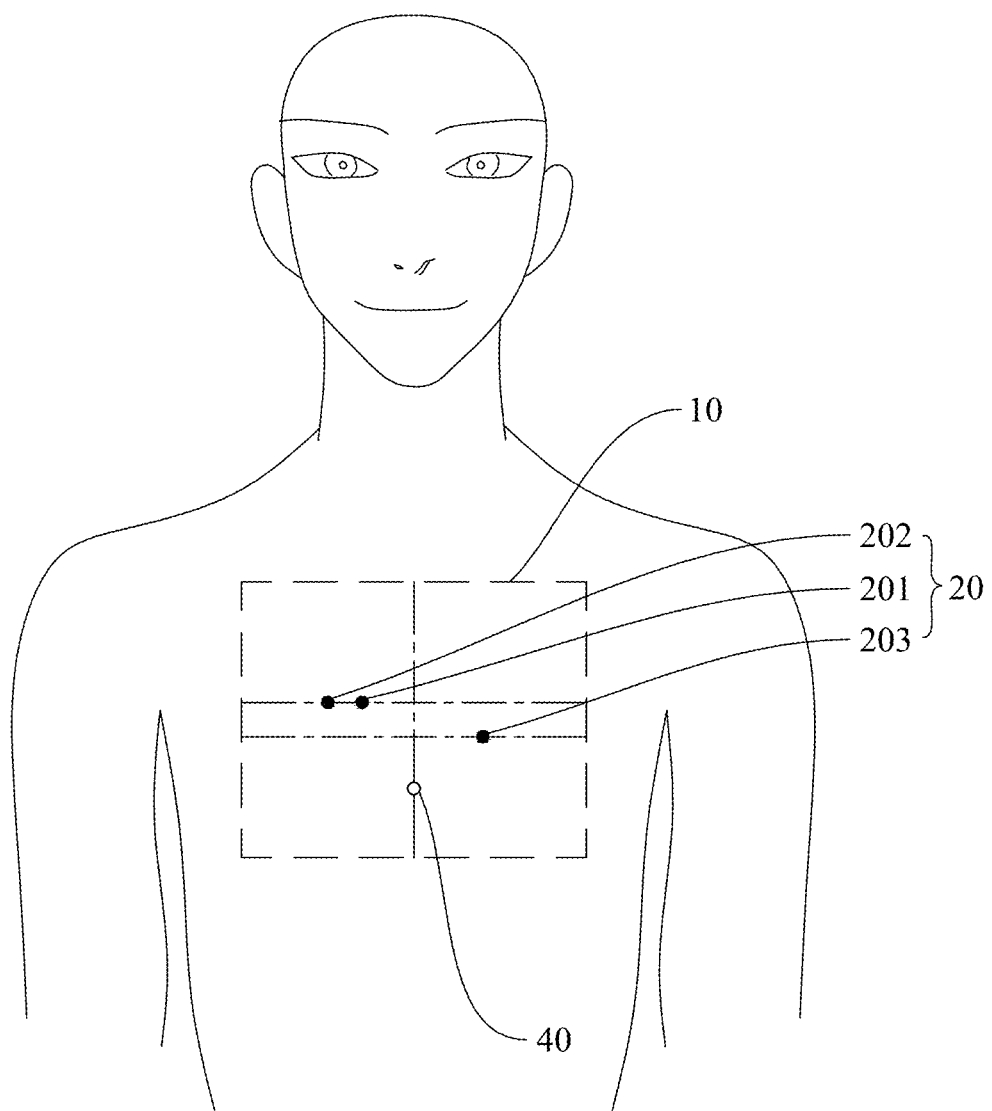
FIG. 7 shows a method (II) of arranging the electrodes on the electrocardiographic monitoring device of the present invention.
Figure 8:
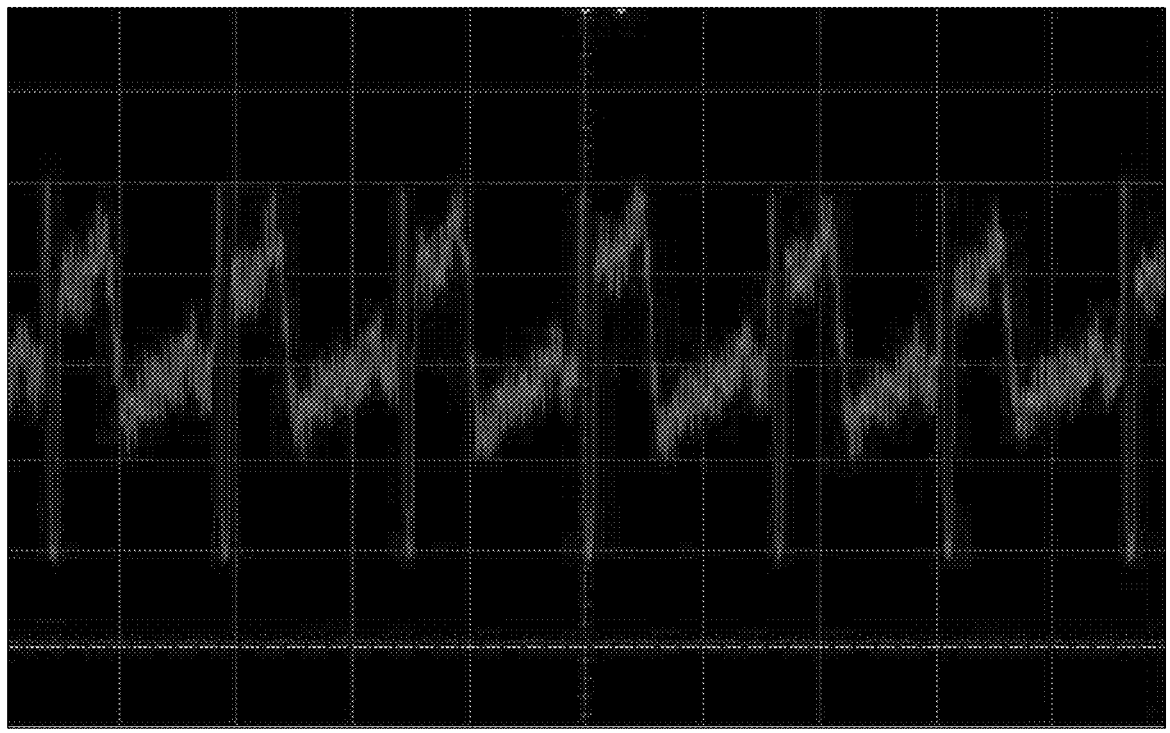
FIG. 8 shows a second group of electrocardiographic signal waveforms resulting from the method (II) of arranging the electrodes on the electrocardiographic monitoring device of the present invention.

In another preferred embodiment as shown in FIG. 7, in which the electrocardiographic monitoring device 100 has been attached to a user's chest, the right electrode (RA) 201 and the grounding electrode (G) 202 are horizontally arranged in an area higher than and to the right of the user's xiphoid process 401 (from the user's point of view), and the left electrode (LA) 203 is higher than and to the left of the user's xiphoid process 401 (also from the user's point of view) and is lower than the right electrode (RA) 201 and the grounding electrode (G) 202. This electrode arrangement produces an electrocardiogram as shown in FIG. 8.

Figure 9:
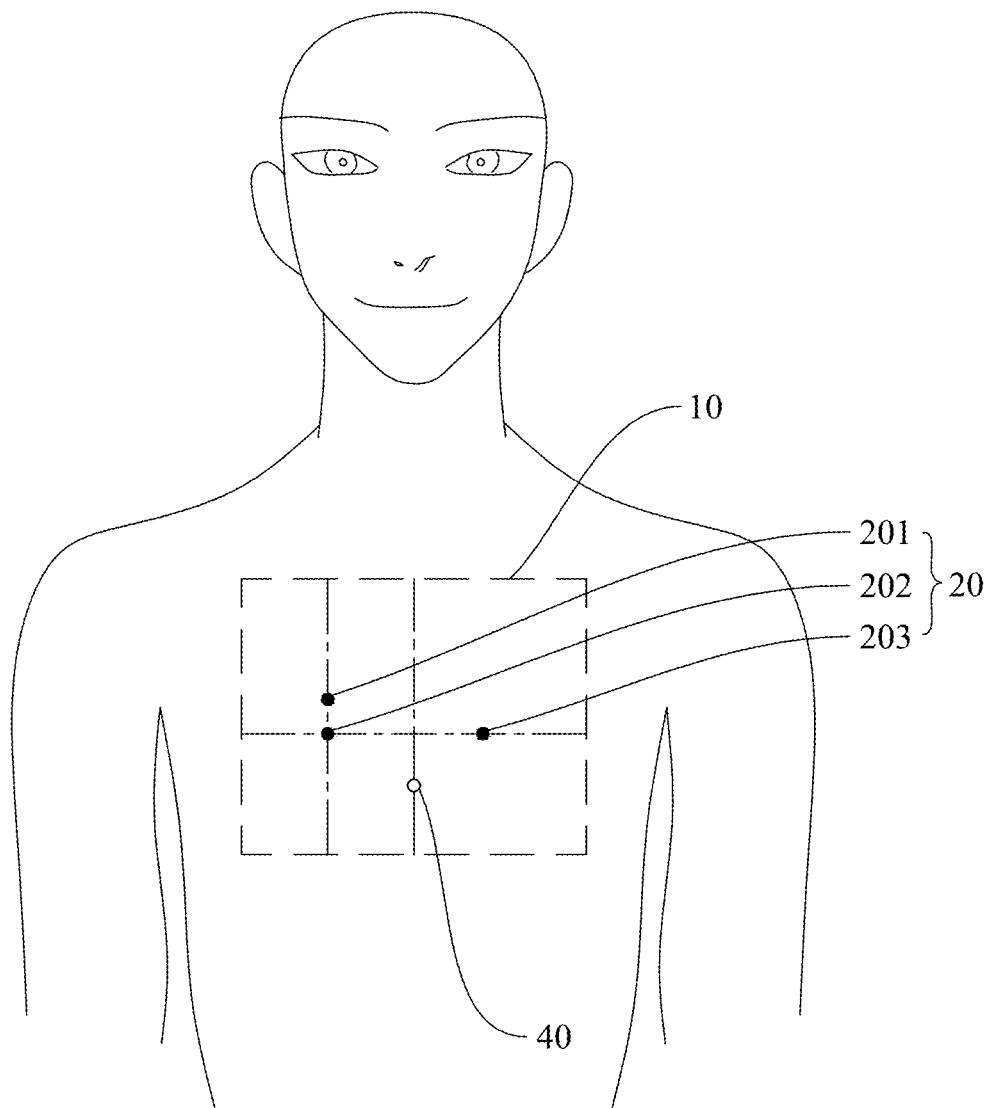
FIG. 9 shows a method (III) of arranging the electrodes on the electrocardiographic monitoring device of the present invention.
Figure 10:
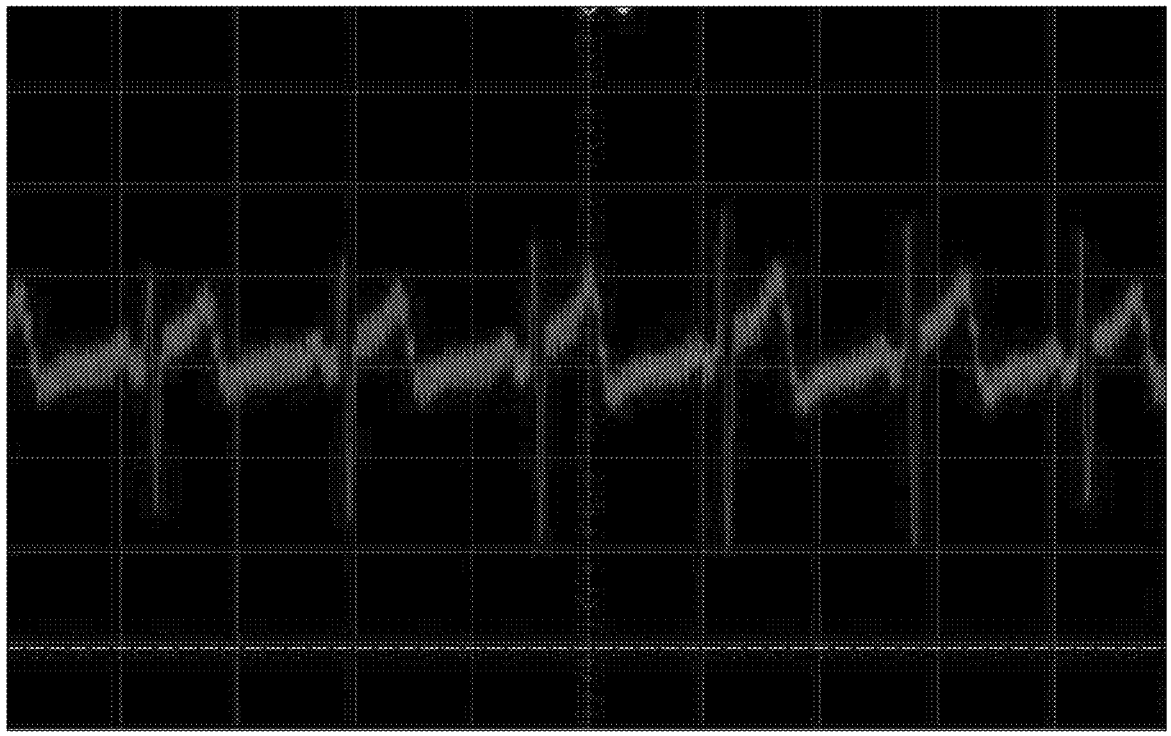
FIG. 10 shows a third group of electrocardiographic signal waveforms resulting from the method (III) of arranging the electrodes on the electrocardiographic monitoring device of the present invention.

In yet another preferred embodiment as shown in FIG. 9, in which the electrocardiographic monitoring device 100 has been attached to a user's chest, the right electrode (RA) 201 and the grounding electrode (G) 202 are vertically arranged in an area higher than and to the right of the user's xiphoid process 401 (from the user's point of view), with the right electrode (RA) 201 higher than the grounding electrode (G) 202, and the left electrode (LA) 203 is higher than and to the left of the user's xiphoid process 401 (also from the user's point of view) and is horizontally aligned with the grounding electrode (G) 202. This electrode arrangement produces an electrocardiogram as shown in FIG. 10.

Figure 11:
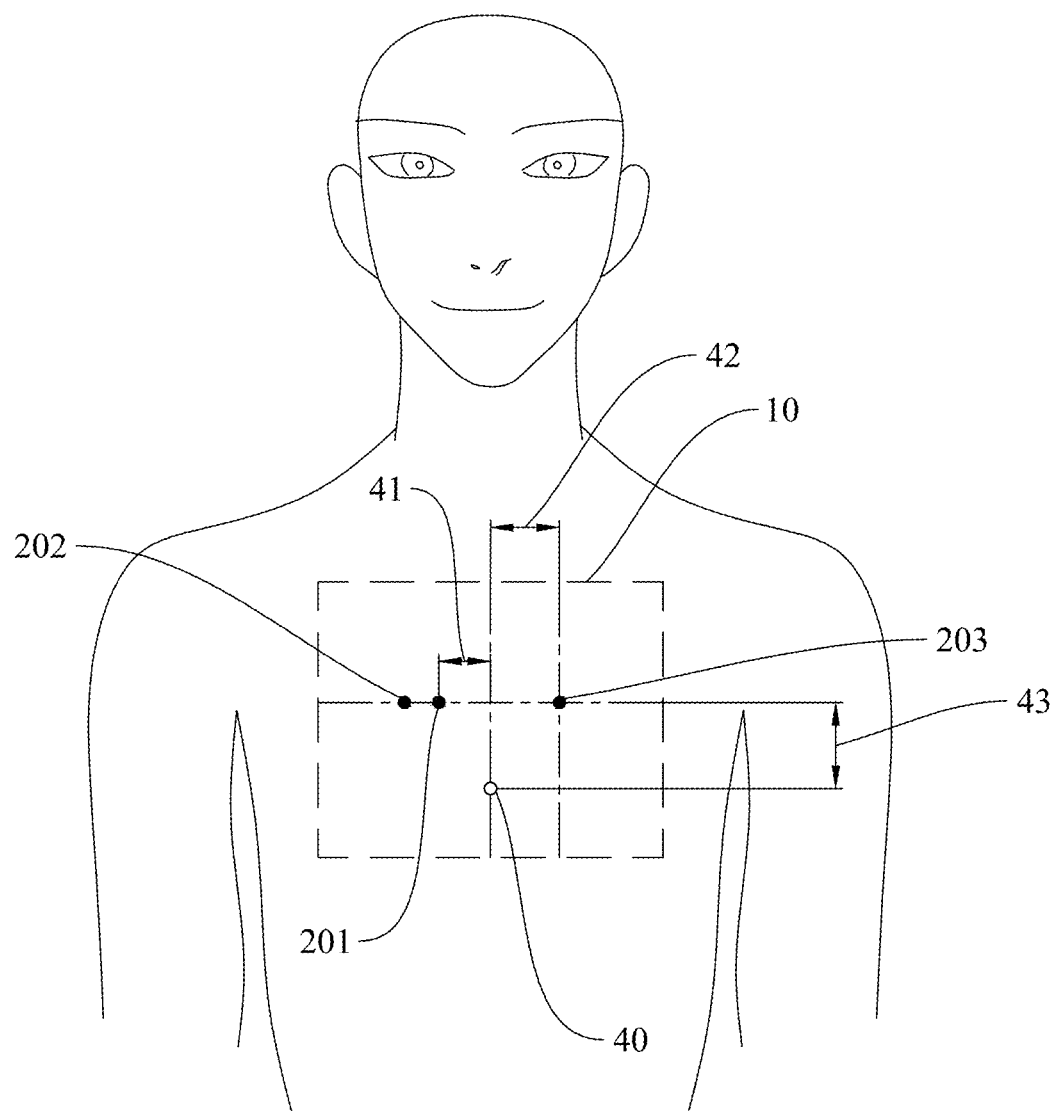
FIG. 11 shows the distance between the right electrode (RA) and the centerline of the user's body, and between the left electrode (LA) and the centerline of the user's body.

In the embodiments described above, the actual positions of the right electrode (RA) 201 (located higher than and to the right of the user's xiphoid process 401, from the user's point of view) and of the left electrode (LA) 203 (located higher than and to the left of the user's xiphoid process 401, also from the user's point of view) may vary with the size of the user's chest. Generally, referring to FIG. 11, the horizontal distance 41 between the right electrode (RA) 201 and the centerline of the user's body is about 10~60 mm, the horizontal distance 42 between the left electrode (LA) 203 and the centerline of the user's body is about 10~60 mm, and the vertical distance from the right electrode (RA) 201 and the left electrode (LA) 203 to the user's xiphoid process 401 is about 50~100 mm. In light of users' individual differences, the distance ranges stated above are by no means limiting.

Figure 3:
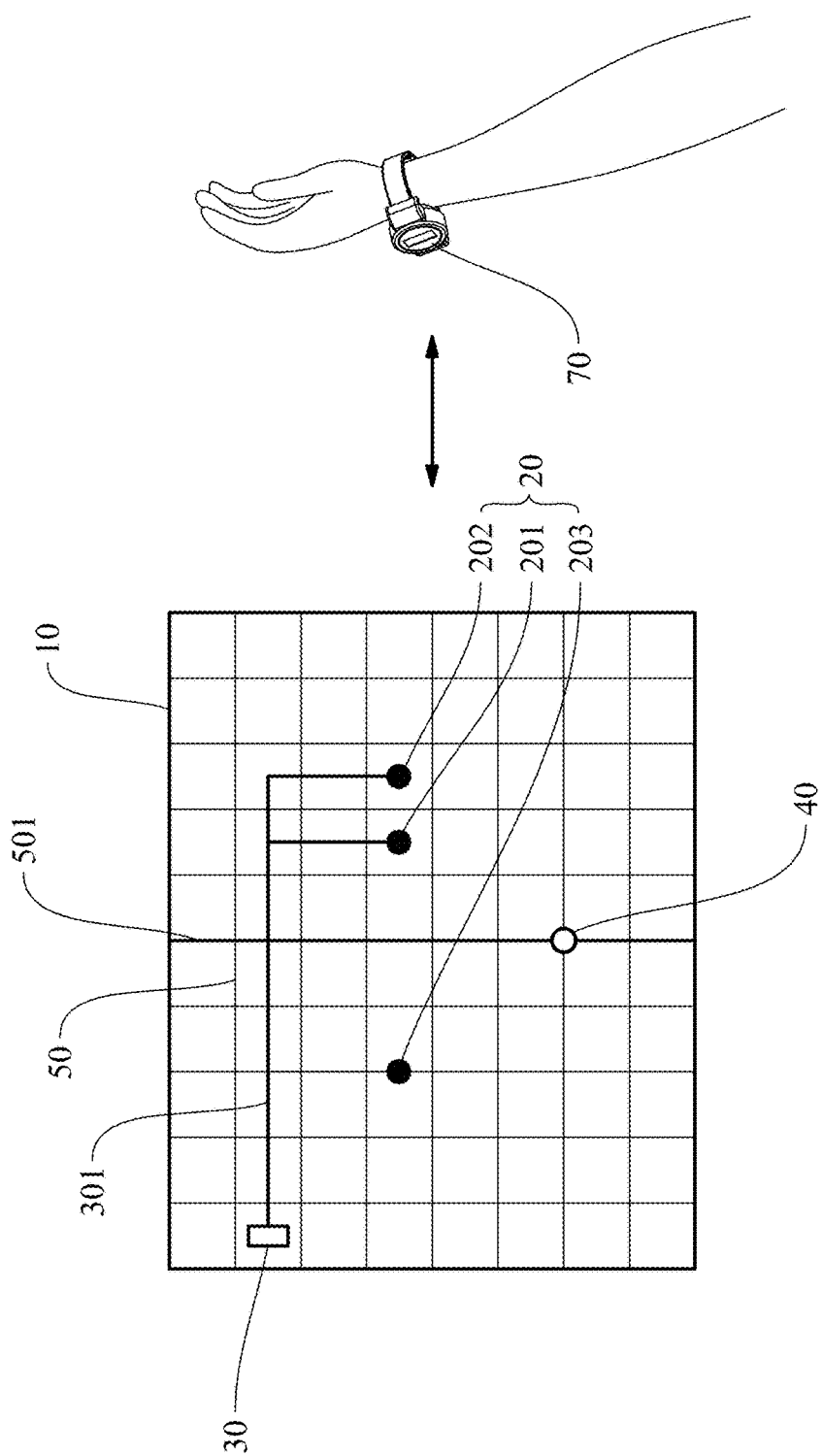
FIG. 3 shows a configuration (I) of an electrocardiographic monitoring device of the present invention and a blood pressure monitoring system using the same.
Figure 4:
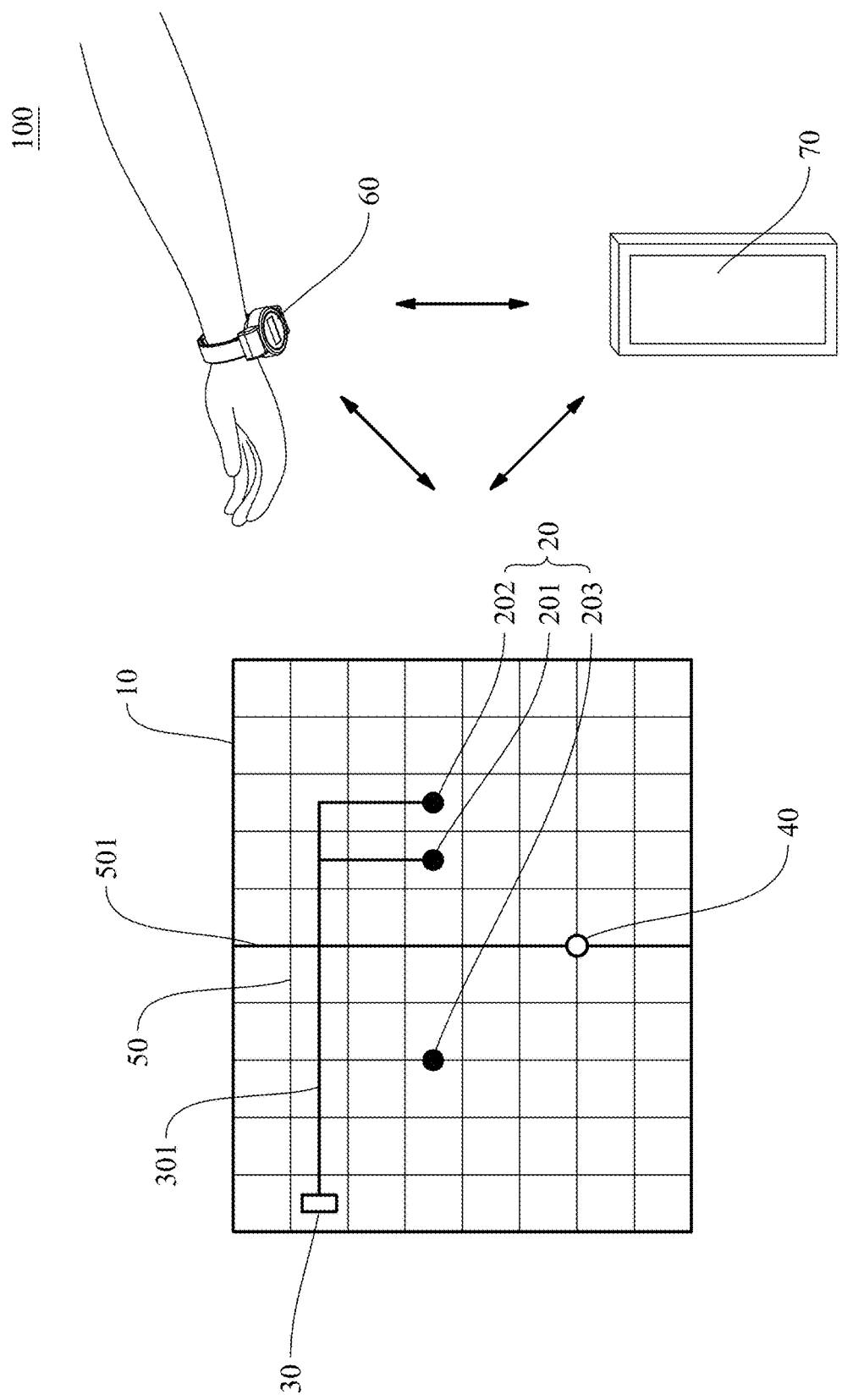
FIG. 4 shows a configuration (II) of an electrocardiographic monitoring device of the present invention and a blood pressure monitoring system using the same.

FIG. 3 and FIG. 4 show two different configurations of a blood pressure monitoring system according to the present invention.

As shown in the drawings, the blood pressure monitoring system 400 includes an electrocardiographic monitoring device 100 and a pulse detection device 60. A controller is provided in at least one selected from the group consisting of the electrocardiographic monitoring device 100, the pulse detection device 60, and a mobile device 70 (in FIG. 3 and FIG. 4 for example, a controller 30 is provided in the electrocardiographic monitoring device 100) and is configured to calculate a user's blood pressure parameters according to electrocardiographic signal waveforms and pulse signal waveforms. In other words, any one or two or all of the electrocardiographic monitoring device 100, the pulse detection device 60, and the mobile device 70 may be provided with such a controller. The electrocardiographic monitoring device 100, the pulse detection device 60, and the mobile device 70 are connected to one another through wireless transmission.

The electrocardiographic monitoring device 100 is configured to be attached to a user's chest and includes a device body 10 and a plurality of electrodes 201, 202, and 203. The electrodes are provided on the device body 10 to obtain electrocardiographic signal waveforms. For example, the electrocardiographic monitoring device 100 is the electrocardiographic monitoring device disclosed above, and the electrodes 201, 202, and 203 may be arranged in any of the foregoing manners.

The pulse detection device 60 in this embodiment is in the form of a watch, but it is also feasible to implement the pulse detection device 60 as a health bracelet or sports bracelet instead of a watch; the present invention has no limitation in this regard.

The mobile device 70 in this embodiment is in the form of a mobile phone, but it is also feasible to implement the mobile device 70 as a tablet computer or laptop computer instead of a mobile phone; the present invention has no limitation in this regard either.

The wireless transmission connection may use one or a combination of the following protocols/techniques: Bluetooth, infrared (IR) transmission, near-field communication (NFC), ultra-wideband (UWB), wireless local area networks (WLAN), Wireless Gigabit Alliance (WiGig Alliance) communications technology, ZigBee, wireless universal serial bus (wireless USB), and Wi-Fi; the present invention has no limitation in this regard.

In addition, the controller 30, the pulse detection device 60, and the mobile device 70 may be provided with a storage unit for recording electrocardiographic signal waveforms, pulse signal waveforms, and/or blood pressure parameters. The storage unit may be a memory card or other devices with a memory function, such as a compact flash card (CF card), a secure digital card (SD card), a multimedia card, a smart media card (SM card), a memory stick (MS card), or a mini secure digital card (mini SD card). The present invention has no limitation on the type of the storage unit.

According to the present invention, blood pressure parameters are derived from the relationship between pulse wave velocity from the heart and pulse pressure at the wrist, and the derivation process entails pulse wave velocity and correction parameters. The term "blood pressure" refers to diastolic pressure, systolic pressure, and/or mean arterial pressure. In the present invention, mean arterial pressure can be calculated by any applicable method without limitation. In one preferred embodiment, mean arterial pressure is determined by the following equation (I):

$$\text{mean arterial pressure (MAP)} = a \cdot \left(\frac{L}{T_{PA}} \times c\right) + b \qquad (I)$$

where L is the length of the path along which an arterial pulse propagates from the aortic orifice in the heart through the arm to the radial artery in the wrist; $T_{PA}$ is the pulse arrival time; and a, b, and c are correction parameters. The pulse arrival time is obtained as the time difference between an R-wave peak value of an electrocardiographic signal and the corresponding peak value of the corresponding pulse signal, or as the time difference between an R-wave valley value of an electrocardiographic signal and the corresponding valley value of the corresponding pulse signal. The correction parameter a ranges from 0.01 to 0.15 and may be, but is not limited to, 0.01, 0.02, 0.03, 0.04, 0.05, 0.06, 0.07, 0.08, 0.09, 0.10, 0.11, 0.12, 0.13, 0.14, or 0.15. The correction parameter b ranges from 0.01 to 0.15 and may be, but is not limited to, 0.01, 0.03, 0.05, 0.07, 0.09, 0.11, 0.13, or 0.15. The correction parameter c ranges from 1 to 1000 and may be, but is not limited to, 1, 10, 100, or 1000. In a more preferred embodiment, the correction parameter a ranges from 0.02 to 0.04, the correction parameter b ranges from 0.02 to 0.04, and the correction parameter c is 1.

In another preferred embodiment, mean arterial pressure is determined by the following equation (II):

$$\text{mean arterial pressure (MAP)} = A \cdot \left(\frac{L_P}{T_{PA}} + C\right)^2 + B \qquad (II)$$

where L is the length of the path along which an arterial pulse propagates from the aortic orifice in the heart through the arm to the radial artery in the wrist; $T_{PA}$ is the pulse arrival time; and A, B, and C are correction parameters. The pulse arrival time is obtained as the time difference between an R-wave peak value of an electrocardiographic signal and the corresponding peak value of the corresponding pulse signal, or as the time difference between an R-wave valley value of an electrocardiographic signal and the corresponding valley value of the corresponding pulse signal. The correction parameter A ranges from 0.01 to 0.15 and may be, but is not limited to, 0.01, 0.02, 0.03, 0.04, 0.05, 0.06, 0.07, 0.08, 0.09, 0.10, 0.11, 0.12, 0.13, 0.14, or 0.15. The correction parameter B ranges from 0.1 to 1.0 and may be, but is not limited to, 0.1, 0.2, 0.3, 0.4, 0.5, 0.6, 0.7, 0.8, 0.9, or 1.0. The correction parameter C ranges from 1 to 1000 and may be, but is not limited to, 1, 10, 100, or 1000.

To sum up, the electrocardiographic monitoring device of the present invention is a structure with a plurality of electrodes and is configured for wireless transmission. Once the electrocardiographic monitoring device is attached to a user's chest, the electrodes will not shift in position due to the user's movement, so the waveforms of electrocardiographic signals will not be affected when the user moves. Furthermore, the electrodes of the electrocardiographic monitoring device of the present invention are so arranged as to avoid serious noise interference typical of the conventional electrode arrangement (e.g., the R-wave peak values of an electrocardiographic signal resulting from the conventional electrode arrangement are subject to noise interference and hence may not be clearly detected, which in turn makes it impossible to measure pulse wave velocity, let alone blood pressure values). In addition, the electrocardiographic monitoring device of the present invention and a blood pressure monitoring system using the same can transmit electrocardiographic signal waveforms and pulse signal waveforms to a blood pressure calculation unit wirelessly; therefore, the wires conventionally required for data transmission can be dispensed with, which not only spares users the discomfort of those wires, but also prevents unstable data transmission, and consequently inaccurate blood pressure measurement, as may otherwise occur if the wires got caught. Moreover, the electrocardiographic monitoring device of the present invention and a blood pressure monitoring system using the same can provide 24-hour monitoring of blood pressure variation and are suitable for use at home as well as in emergency rooms, hospital wards, intensive care units, clinics, and other medical institutions.

The above is the detailed description of the present invention. However, the above is merely the preferred embodiment of the present invention and cannot be the limitation to the implement scope of the present invention, which means the variation and modification according to the present invention may still fall into the scope of the invention.

What is claimed is:

1. A monitoring system, comprising:
a monitoring device, the monitoring device comprising:
a device body configured to be attached to a user's chest;
a plurality of electrodes provided on the device body, wherein the electrodes comprise a right electrode (RA), a left electrode (LA), and a grounding electrode (G), the right electrode and the left electrode are provided on a right side and a left side of the device body respectively, and the grounding electrode is adjacent to the right electrode but is not between the right electrode and the left electrode; and
a controller provided on the device body and connected to the electrodes in order to obtain the user's electrocardiographic signal waveforms;
wherein the device body further comprises a positioning mark and a grid, the positioning mark is intended to coincide with the user's xiphoid process, the grid includes a vertical auxiliary line passing through the positioning mark, and the vertical auxiliary line is intended to align with the centerline of the user's body;
wherein the grid comprises the electrodes and the positioning mark which are disposed on the grid, and the grid is configured to be attached so that the electrodes and the positioning mark are provided at the recited positions;
wherein the electrocardiographic monitoring device is configured to be attached to a user's chest, the right electrode (RA) and the grounding electrode (G) are configured to be horizontally arranged in an area higher than and to the right of the user's xiphoid process, and the left electrode (LA) is configured to be higher than and to the left of the user's xiphoid process and is horizontally aligned with the right electrode (RA) and the grounding electrode (G);
wherein the horizontal distance between the right electrode (RA) and the vertical auxiliary line is 10~60 mm, the horizontal distance between the left electrode (LA) and the vertical auxiliary line is 10~60 mm, and the vertical distance from the right electrode (RA) and the left electrode (LA) to the positioning mark is 50~100 mm.

2. The monitoring system of claim 1, further comprising:
a pulse detection device configured to be worn on a user's limb at a position corresponding to a radial artery, wherein the pulse detection device comprises a sensor for obtaining pulse signal waveforms;
wherein the pulse detection device, or a mobile device is provided with another controller for calculating the user's blood pressure parameters according to the user's electrocardiographic signal waveforms and the pulse signal waveforms; and wherein the controller on the device body, the pulse detection device, and the mobile device are connected to one another through wireless transmission.

3. The monitoring system of claim 2, wherein the blood pressure parameters is a mean arterial pressure, and the mean arterial pressure is determined by the following equation (I):

$$\text{mean arterial pressure } (MAP) = a \cdot \left( \frac{L}{T_{PA}} \times c \right) + b, \quad (I)$$

where L is the length of the path along which an arterial pulse propagates from the aortic orifice in the heart through the arm to the radial artery in the wrist; $T_{PA}$ is the pulse arrival time; and a, b, and c are correction parameters.

4. A monitoring system, comprising:
a monitoring device, the monitoring device comprising:
a device body configured to be attached to a user's chest;
a plurality of electrodes provided on the device body, wherein the electrodes comprise a right electrode (RA), a left electrode (LA), and a grounding electrode (G), the right electrode and the left electrode are provided on a right side and a left side of the device body respectively, and the grounding electrode is adjacent to the right electrode but is not between the right electrode and the left electrode; and
a controller provided on the device body and connected to the electrodes in order to obtain the user's electrocardiographic signal waveforms;
wherein the device body further comprises a positioning mark and a grid, the positioning mark is intended to coincide with the user's xiphoid process, the grid includes a vertical auxiliary line passing through the positioning mark, and the vertical auxiliary line is intended to align with the centerline of the user's body;
wherein the grid comprises the electrodes and the positioning mark which are disposed on the grid, and the grid is configured to be attached so that the electrodes and the positioning mark are provided at the recited positions;
wherein the electrocardiographic monitoring device is configured to be attached to a user's chest, the right electrode (RA) and the grounding electrode (G) are configured to be horizontally arranged in an area higher than and to the right of the user's xiphoid process, and the left electrode (LA) is configured to be higher than and to the left of the user's xiphoid process and is lower than the right electrode (RA) and the grounding electrode (G);
wherein the horizontal distance between the right electrode (RA) and the vertical auxiliary line is 10~60 mm, the horizontal distance between the left electrode (LA) and the vertical auxiliary line is 10~60 mm, and the vertical distance from the right electrode (RA) and the left electrode (LA) to the positioning mark is 50~100 mm.

5. The monitoring system of claim 4, further comprising:
a pulse detection device configured to be worn on a user's limb at a position corresponding to a radial artery, wherein the pulse detection device comprises a sensor for obtaining pulse signal waveforms;
wherein the pulse detection device, or a mobile device is provided with another controller for calculating the user's blood pressure parameters according to the user's electrocardiographic signal waveforms and the pulse signal waveforms; and wherein the controller on the device body, the pulse detection device, and the mobile device are connected to one another through wireless transmission.

6. The monitoring system of claim 5, wherein the blood pressure parameters is a mean arterial pressure, and the mean arterial pressure is determined by the following equation (I):

$$\text{mean arterial pressure } (MAP) = a \cdot \left( \frac{L}{T_{PA}} \times c \right) + b, \quad (I)$$

where L is the length of the path along which an arterial pulse propagates from the aortic orifice in the heart through the arm to the radial artery in the wrist; $T_{PA}$ is the pulse arrival time; and a, b, and c are correction parameters.

7. A monitoring system, comprising:

a monitoring device, the monitoring device comprising:

a device body configured to be attached to a user's chest;

a plurality of electrodes provided on the device body, wherein the electrodes comprise a right electrode (RA), a left electrode (LA), and a grounding electrode (G), the right electrode and the left electrode are provided on a right side and a left side of the device body respectively, and the grounding electrode is adjacent to the right electrode but is not between the right electrode and the left electrode; and a controller provided on the device body and connected to the electrodes in order to obtain the user's electrocardiographic signal waveforms;

wherein the device body further comprises a positioning mark and a grid, the positioning mark is intended to coincide with the user's xiphoid process, the grid includes a vertical auxiliary line passing through the positioning mark, and the vertical auxiliary line is intended to align with the centerline of the user's body;

wherein the grid comprises the electrodes and the positioning mark which are disposed on the grid, and the grid is configured to be attached so that the electrodes and the positioning mark are provided at the recited positions;

wherein the electrocardiographic monitoring device is configured to be attached to a user's chest, the right electrode (RA) and the grounding electrode (G) are configured to be vertically arranged in an area higher than and to the right of the user's xiphoid process, with the right electrode (RA) higher than the grounding electrode (G), and the left electrode (LA) is configured to be higher than and to the left of the user's xiphoid process and is horizontally aligned with the grounding electrode (G);

wherein the horizontal distance between the right electrode (RA) and the vertical auxiliary line is 10~60 mm, the horizontal distance between the left electrode (LA) and the vertical auxiliary line is 10~60 mm, and the vertical distance from the right electrode (RA) and the left electrode (LA) to the positioning mark is 50~100 mm.

8. The monitoring system of claim 7, further comprising:

a pulse detection device configured to be worn on a user's limb at a position corresponding to a radial artery, wherein the pulse detection device comprises a sensor for obtaining pulse signal waveforms;

wherein the pulse detection device, or a mobile device is provided with another controller for calculating the user's blood pressure parameters according to the user's electrocardiographic signal waveforms and the pulse signal waveforms; and wherein the controller on the device body, the pulse detection device, and the mobile device are connected to one another through wireless transmission.

9. The monitoring system of claim 8, wherein the blood pressure parameters is a mean arterial pressure, and the mean arterial pressure is determined by the following equation (I):

$$\text{mean arterial pressure } (MAP) = a \cdot \left(\frac{L}{T_{PA}} \times c\right) + b, \qquad (I)$$

where L is the length of the path along which an arterial pulse propagates from the aortic orifice in the heart through the arm to the radial artery in the wrist; $T_{PA}$ is the pulse arrival time; and a, b, and c are correction parameters.

* * * * *